United States Patent [19]

Pieper

[11] Patent Number: 4,587,334

[45] Date of Patent: May 6, 1986

[54] PROCESS FOR MAKING CYANURIC ACID

[75] Inventor: Werner Pieper, Kerpen, Fed. Rep. of Germany

[73] Assignee: Hoechst Aktiengesellschaft, Fed. Rep. of Germany

[21] Appl. No.: 695,265

[22] Filed: Jan. 28, 1985

[30] Foreign Application Priority Data

Feb. 11, 1984 [DE] Fed. Rep. of Germany ....... 3404873

[51] Int. Cl.⁴ ........................................... C07D 251/32
[52] U.S. Cl. ................................................. 544/192
[58] Field of Search .......................................... 544/192

[56] References Cited

U.S. PATENT DOCUMENTS

| | | | |
|---|---|---|---|
| 2,712,491 | 7/1955 | Boatright | 544/192 |
| 3,154,545 | 10/1964 | Symes et al. | 544/192 |
| 3,761,474 | 9/1973 | Mesiah | 544/192 |
| 3,810,891 | 5/1974 | Lee | 544/192 |
| 3,953,443 | 4/1976 | Ohata et al. | 544/192 |
| 4,474,957 | 10/1984 | Sato et al. | 544/192 |

*Primary Examiner*—John M. Ford
*Attorney, Agent, or Firm*—Connolly and Hutz

[57] ABSTRACT

The disclosure relates to a process for making granulated cyanuric acid. To this end, the disclosure provides for cyanuric acid granules having the particle size targeted for the final product to be used as feed material, for the said feed material, urea and water to be used in a ratio by weight of 1.5–3:1:0.04–0.08 and to be made into a preliminary mixture, and for the mixture to be allowed to stand over a period of 10 to 20 hours prior to heating it with continuous agitation to temperatures of 270° to 340° C. over as long a period as necessary to effect the condensation of the urea to cyanuric acid.

2 Claims, No Drawings

PROCESS FOR MAKING CYANURIC ACID

The present invention relates to a process for making granulated cyanuric acid by reacting urea with previously produced cyanuric acid in the presence of water.

Cyanuric acid (HNCO)$_3$ is made commercially by subjecting urea to thermal condensation in accordance with the following reaction equation:

$$3H_2N-\overset{O}{\underset{\|}{C}}-NH_2 \longrightarrow (HNCO)_3 + 3NH_3$$

The condensation can be effected with the aid of an inert solvent (wet process) or in substance (dry process) (cf. Ullmanns Enzyklopädie der technischen Chemie, 4th edition, volume 9, page 647 (1975)).

A disadvantage which is associated with the wet processes resides in the fact that it is always necessary for the crude cyanuric acid to be separated from the solvent naturally with additional work and expenditure due to the loss of solvent etc.

No such problem is associated with the dry processes which make it necessary however to provide means preventing the material to undergo reaction from caking together during the reaction, during which the physical state of the condensation products changes from liquid to highly viscous to solid, as the reaction time goes on. In view of the fact that the resulting ill heat-conducting solid material is liable to deposit on the heating surfaces, the condensation comes to a standstill and final product containing little cyanuric acid is obtained. To remedy this deficiency, it has been suggested that urea or another suitable preliminary product, such as biuret, or urea cyanurate should be used and reacted in the form of a thin layer, e.g. on a heated belt or in a rotating drum (U.S. Pat. No. 30 93 641 or on a metal melt (German Pat. No. 1 065 420). Further processes provide for an inert solid diluent, such as cyanuric acid, to be used, and for the reaction to be carried out in a rotating furnace (U.S. Pat. No. 2,943,088) or in a fluidized bed (U.S. Pat. No. 3,394,136). In these processes, cyanuric acid is recycled as this has the technically beneficial effect that the system remains free from foreign substances, for which it would be necessary to be subsequently separated therefrom.

Apart from biuret and triuret which are products forming during stages preliminary to the formation of cyanuric acid, the crude cyanuric acid obtained in the processes referred to above contains varying proportions of cyanuric acid amides, such as ammelide, ammeline and melamine, which reduce the cyanuric acid yield and which must subsequently be removed by subjecting them to treatment with an acid or must be hydrolyzed to give cyanuric acid.

In order to avoid such acid treatment and yet to obtain crude cyanuric acid with a quality permitting the crude product to be chlorinated to chloroisocyanates, the educt mixture has previously been admixed with a catalyst, such as ammonium nitrate or nitric acid (cf. DE-OS No. 27 56 579).

In DE-OS No. 27 56 579, the presence of 5% water, based on the feed weight of urea, is said to be indeed allowable for the reaction mixture, but it has not been recognized heretofore that it is possible by the combined use of a feed product containing a certain amount of water and certain defined processing steps critically to simplify and improve the production of cyanuric acid.

As has unexpectedly been found, it is possible for the urea melt and catalyst used heretofore as the feed material to be replaced by a mixture having been (a) prepared from previously granulated cyanuric acid presenting the particle size targeted for the final product, from urea and water in a ratio by weight of 1.5–3:1:0.04–0.08, preferably 2:1:0.05; (b) allowed to stand over a period of 10 to 20 hours and (c) heated with continuous agitation to temperatures of 270°–340° C. over as long a period as necessary to effect the condensation of the urea to cyanuric acid. The step of heating the mixture can be effected in a tube furnace and at atmospheric pressure. The feed cyanuric acid should preferably consist of particles with a size of 0.2–2 mm.

The tube furnace is, for example, a rotary tube furnace or a stationary heated tube through which the material to undergo reaction is passed using a screw or helix. The feed cyanuric acid which should conveniently be used is recycled cyanuric acid which in accordance with this invention is already in the form of granules with a size desirable for the reaction. Use should conveniently be made of a customary dosing feeder, e.g. a dosing screw, for continuously admitting the mixture of cyanuric acid, urea and water to the heating system in which a temperature gradient may well be established along the heating path. Thus, for example, it is possible to establish a temperature of 270° C. in the head end portion, and a temperature of 340° C. in the tail end portion of the heating system. Lower temperatures, within the limits specified, result in a lower conversion rate or have longer residence times associated therewith. The reaction period is approximately between 5 and 60 minutes. Ecological reasons make it desirable for the cyanuric acid and urea to be used in the smallest possible ratio for which it is not allowable however to be excessively low as the reaction tube is then more likely to undergo encrustation. If no water is added during the reaction, a good deal of the furnace charge is liable to undergo agglomeration; the heating system becomes encrusted and clogged rather soon unless the encrustations are removed mechanically. Only 30–40% of the product is then obtained in the form of desirable granules. By the addition of about 5 weight % water, based on the urea used, it is possible to increase the proportion of desirable granules in the final product to 80% up to more than 90% with the inside walls of the heating tube remaining substantially free from encrustations. It is more particularly desirable to have a high proportion of fine granules in the final product as these undergo conversion at a higher rate than coarse agglomerates during work-up, for example. The addition of less than 3% water, based on the weight of the urea used, is practically ineffective whereas the addition of more than 8 weight % water entails no further beneficial effect.

It is good practice to support the flow of the ammonium/steam-mixture formed during the condensation by means of a slight stream of inert gas which additionally permits the relatively cool inlet zone of the heating system to be kept free from condensate.

The process of this invention and its technically beneficial effects are illustrated in the following examples.

EXAMPLE 1

A stainless steel tube 120 cm long and 2 cm wide was heated using two electric furnaces I and II. Furnace I was used for maintaining the inlet zone (40 cm long) of the tube at 270° C., whilst furnace II was used for maintaining the directly adjoining zone (60 cm long) at 340° C., so that the heating path was 100 cm long. A helix presenting a lead of 2 cm per winding placed freely rotatable in the reaction tube was arranged to be motor-driven at a speed of 4 rpm. By means of a piston dosing pump, 4.8 g per min.$^{-1}$ educt mixture consisting of 578 g granulated cyanuric acid (particle size=0.2-2 mm) and 298 g urea were introduced into the tube. The residence time of the educt mixture in the reaction system was theoretically 12.5 minutes, but really was 20-30 minutes due to the occurrence of remixing phenomena. 671 g product was separated of which only 36% consisted of particles with a size of 0.2-2 mm, whilst the bulk was found to have caked together to coarse agglomerates. The fine particles contained 96.4% cyanuric acid and the coarse particles contained 94.9% cyanuric acid and 1.6% ammelide/ammeline.

97 g of encrusted product was found to have been retained in the reaction tube.

EXAMPLE 2

582 g cyanuric acid the same as that used in Example 1, 291 g urea and 14.6 g water are mixed and immediately thereafter introduced into the reaction tube at a rate of 3 g per min$^{-1}$. The reaction conditions were as in Example 1. 718 g final product was separated of which 77 weight % consisted of particles with a size of less than 2 mm, which contained 96 weight % cyanuric acid and 1.5 weight % ammelide. 49 g product was found to have been retained in the reaction tube.

EXAMPLE 3

As described in Example 2, 382 g cyanuric acid (particle size=0.2-2 mm), 191 g urea and 9.6 g water were mixed and 20 hours later introduced into the reaction tube at a rate of 4.7 g per min$^{-1}$. The screw conveyor in the tube was caused to rotate at a speed of 4 rpm. 475 g final product was separated of which 95 weight % consisted of particles with a size of 0.2 to 2 mm. The product contained 96 weight % cyanuric acid and 2 weight % ammelide.

19 g encrusted product was found to have been retained in the reaction tube.

EXAMPLE 4

As described in Example 2, 285 g cyanuric acid, 142 g urea and 7 g water were mixed and 15 hours later introduced into the reaction tube at a rate of 3.1 g per min. The screw conveyor was caused to rotate at a speed of 20 rpm. The residence time of the product in the tube was about 5 minutes. 334 g final product was separated and 24 g encrusted product was found to have been retained in the tube. The product contained 98% cyanuric acid and 0.8% ammelide.

EXAMPLE 5

By means of a dosing screw, 2.8 kg per h$^{-1}$ educt mixture was introduced into an electrically heated rotating tube 2.9 m long and 22 cm wide. The tube was inclined at an angle of 5° and the heated zone was 1.8 m long. The outside temperature of the tube was 320° C. at the head end portion and 380° C. at the tail end portion. The temperature determined for the material admitted to the tube was 240° C. in the tube center portion. The tube rotated at a speed of 2 rpm.

Upon the introduction of an anhydrous educt mixture of cyanuric acid and urea in a ratio by weight of 2:1, the rotating tube was found to become clogged after an introduction period of 30 minutes by material encrusting in the head portion of the thermolysis zone; upon the use of a mixture consisting of cyanuric acid, urea and water in a ratio of 2:1:0.05, the reaction zone remained substantially free from encrustations. 14 kg educt mixture was used and 11.6 kg product containing 99% cyanuric acid was separated; ammelide could not be detected gravimetrically. 95% of the product consisted of particles with a size of less than 2 mm.

I claim:

1. In the process for making cyanuric acid by heating urea with previously produced cyanuric acid, which comprises:
   (a) using as starting material granulated cyanuric acid having the particle size targeted for the final product;
   (b) making the said cyanuric acid, urea and water in a ratio by weight of 1.5-3:1:0.04-0.08 into a preliminary mixture, and
   (c) allowing the said mixture to stand over a period of 10 to 20 hours; thereafter heating said mixture with continuous agitation to temperature of 270° to 340° C. over as long a period as necessary to effect the condensation of the urea to cyanuric acid, with the resultant formation of granulated cyanuric acid.

2. The process as claimed in claim 1, wherein a mixture of cyanuric acid, urea and water in a ratio by weight of 2:1:0.05 is used.

* * * * *